United States Patent [19]

Pentling et al.

[11] Patent Number: 5,386,067
[45] Date of Patent: Jan. 31, 1995

[54] PROCESS FOR SEPARATING MIXTURES OF M- AND P-DICHLOROBENZENE

[75] Inventors: Ursula Pentling, Kempen; Hans-Josef Buysch, Krefeld; Lothar Puppe, Burscheid; Kai Röhlk, Bergisch Gladbach; Rolf Grosser, Leverkusen; Hans-Ingolf Paul, Köln, all of Germany

[73] Assignee: Bayer Aktiengesellschaft, Leverkusen, Germany

[21] Appl. No.: 252,154

[22] Filed: Jun. 1, 1994

Related U.S. Application Data

[63] Continuation of Ser. No. 71,739, Jun. 3, 1993, abandoned.

[30] Foreign Application Priority Data

Jun. 9, 1992 [DE] Germany .................. 4218841

[51] Int. Cl.$^6$ .......................................... C07C 17/38
[52] U.S. Cl. .................................................. 570/211
[58] Field of Search ...................................... 570/211

[56] References Cited

U.S. PATENT DOCUMENTS

| | | |
|---|---|---|
| 4,300,004 | 11/1981 | Wissner et al. |
| 4,571,441 | 2/1986 | Miwa et al. |
| 4,873,383 | 10/1989 | Toshitaka ............ 510/211 |
| 4,996,380 | 2/1991 | McCulloch et al. |

FOREIGN PATENT DOCUMENTS

| | | |
|---|---|---|
| 0012891 | 9/1981 | European Pat. Off. |
| 0278680 | 8/1988 | European Pat. Off. |
| 0334025 | 9/1989 | European Pat. Off. |
| 2175433 | 8/1984 | Japan ............ 570/211 |
| 1268636 | 11/1986 | Japan ............ 570/211 |

OTHER PUBLICATIONS

JP 62/275,433, Industrial Organics, vol. 108, 1988.
JP 58/131,926, Chemical Abstracts, vol. 100, 1984.

*Primary Examiner*—Alan Siegel
*Attorney, Agent, or Firm*—Sprung Horn Kramer & Woods

[57] ABSTRACT

Mixtures of m- and p-dichlorobenzene can be separated by treating such mixtures in the liquid phase with a pentasil zeolite at from 20° to 250° C., a filtrate enriched in m-dichlorobenzene being removed and the p-dichlorobenzene being obtained by desorption of the pentasil zeolite. The pentasil zeolites may contain, as exchangeable cations, protons, cations of the first or second main group of the Mendeleev Periodic System, cations of the rare earth metals or a mixture of a plurality thereof. In order to prepare the liquid phase a solvent is used that belongs to the group of cyclic saturated hydrocarbons having 5 to 15 carbon atoms, alkyl-substituted aromatic hydrocarbons having 8 to 12 carbon atoms, and halogen-substituted aromatic hydrocarbons having 6 to 10 carbon atoms and 1 to 3 halogen atoms. The solvents ethylbenzene, chlorobenzene, p-xylene, p-chlorotoluene and dichlorobenzene are excepted. A mixture of a plurality of these solvents may also be used.

9 Claims, No Drawings

PROCESS FOR SEPARATING MIXTURES OF M- AND P-DICHLOROBENZENE

This application is a continuation of, application Ser. No. 08/071,739, filed Jun. 3, 1993 now abandoned.

BACKGROUND OF THE INVENTION

Field of the Invention

The present invention describes a process for separating mixtures of m- and p-dichlorobenzenes, p-dichlorobenzene being separated from such mixtures and an enriched m-dichlorobenzene being removed. The separation is carried out in the liquid phase on pentasil zeolites in the liquid phase with the use of solvents.

2. Description of the Related Art

In the chlorination of benzene or monochlorobenzene to dichlorobenzene, a mixture of the three isomeric dichlorobenzenes is generally formed. The fraction containing the dichlorobenzenes can easily be separated on account of the different boiling and melting points from the other products in the chlorination mixture, for example the starting substances and higher chlorination products. The separation of the individual dichlorobenzene isomers in this fraction is however difficult and extremely complicated. The dichlorobenzene fraction freed from the by-products is first of all distilled, m- and p-dichlorobenzene being obtained as top product and o-dichlorobenzene being obtained as bottom product. Since m- and p-dichlorobenzene have identical boiling points, the further separation is carried out by fractional crystallisation, a large part of the p-dichlorobenzene being obtained in pure form and an m-dichlorobenzene concentrate remaining behind, which, depending on the degree of crystallisation, contains amounts of from 70 to 80% by weight of m-dichlorobenzene and from 30 to 20% by weight of p-dichlorobenzene (EP 012,891). Also, adsorptive processes for the separation or further separation of mixtures of dichlorobenzenes using molecular sieves are in principle known. For example, EP 334,025 describes the separation of halogenated aromatics on various zeolites in the presence of aromatic hydrocarbons. The separation of m- and p-dichlorobenzene on pentasil zeolites is, however, not disclosed in this description. EP 278,680, JP 62/175,433 (1987) and U.S. Pat. No. 4,996,380 describe the separation of m-dichlorobenzene from mixtures thereof with o- and p-dichlorobenzene without using eluants. These processes are suitable for separating small amounts of m-dichlorobenzene from mixtures containing mainly o- and p-dichlorobenzene. Since, however, an m-dichlorobenzene concentrate is easily obtained in the working-up of technical dichlorobenzene product mixtures by distillation and a simple crystallisation step, from which the contained residues of p-dichlorobenzene can be separated only by time-consuming and energy-consuming distillation and crystallisation steps, a process that permits an economical separation of the p-dichlorobenzene from an m-dichlorobenzene concentrate is extremely desirable.

Such a separation of small amounts of p-dichlorobenzene from mixtures containing mainly m-dichlorobenzene using molecular sieves has not been satisfactorily solved according to the prior art.

U.S. Pat. No. 4,571,441 and JP 58/131924 (1983) describe the separation of p-dichlorobenzene from mixtures containing o- and m-dichlorobenzene using faujasite X and faujasite Y, each of which contain silver, copper, sodium or potassium or a plurality thereof as exchangeable cations. Substituted aromatic hydrocarbons are used as desorbents. The selectivities achieved in these processes are extremely low and do not guarantee an economical process.

SUMMARY OF THE INVENTION

A process has been found for separating mixtures of m- and p-dichlorobenzene by treating such mixtures in the liquid phase with a zeolite, which process is characterised in that the mixture is treated in a solvent from the group of cyclic saturated hydrocarbons having 5 to 15 carbon atoms, alkyl-substituted aromatic hydrocarbons having 8 to 12 carbon atoms, and halogen-substituted aromatic hydrocarbons having 6 to 10 carbon atoms and 1 to 3 halogen atoms or a mixture of a plurality thereof, with the exception of the solvents ethylbenzene, chlorobenzene, p-xylene, p-chlorotoluene and dichlorobenzene, at from 20° to 250° C. with a pentasil zeolite that contains, as exchangeable cations, protons, cations of the first or second main group of the Mendeleev Periodic System, cations of the rare earth metals or a mixture of a plurality thereof, the enriched m-dichlorobenzene is removed as filtrate, and p-dichlorobenzene is obtained by desorption of pentasil zeolites.

DETAILED DESCRIPTION OF THE INVENTION

A process is thereby provided which enables p-dichlorobenzene to be separated very selectively from mixtures containing m-dichlorobenzene. The process according to the invention has the advantage that it can be carried out batchwise in an intermittent process and also continuously in a countercurrent process. The nature and manner of the implementation of these two process variants is known to the person skilled in the art, and as such is not the subject of the present invention.

In the process according to the invention p-dichlorobenzene is separated very selectively from mixtures thereof with m-dichlorobenzene by bringing the mixture of the dichlorobenzene isomers into contact in the liquid phase with zeolites of the pentasil type under adsorption conditions, such as are known in principle to the person skilled in the art.

Zeolites may generally be described by the empirical formula $$M_{2/n}O \cdot Al_2O_3 \cdot xSiO_2 \cdot yH_2O \qquad (I)$$

wherein
- M denotes an exchangeable cation or a mixture of a plurality thereof,
- n denotes the charge of the exchangeable cation,
- x denotes integers from 2 to 2,000, and
- y is the amount of the sorbed water.

The sorbed water phase $yH_2O$ is reversibly removable, without the zeolite skeleton losing its structure.

Of the large number of zeolites known to the person skilled in the art, according to the invention those having the pentasil structure are used.

The following pentasil structure types are preferably used: ZSM 5, ZSM 11, ZSM 8, ZSM 5/ZSM 11-intermediates, Zeta 1, Zeta 3, ZBM 10, Ultrasil, Ultrazet, TZ-01, NU-4, NU-5, AZ-1. Pentasil zeolites and in particular the individually named structure types are known to the person skilled in the art and are described in numerous publications, for example in EP 54,386, EP 65,401, EP 34,727, EP 57,016 and EP 113,116. Particularly preferably used pentasil zeolites are ZSM 5, ZSM 8, ZSM 11 and ZSM 5/ZSM 11-intermediates. Most particularly preferred are pentasil zeolites of the types ZSM 5 and ZSM 11, no restrictions being placed on the $SiO_2/Al_2O_3$ ratio.

As exchangeable cations M the pentasil zeolites may contain the aforementioned cations. Examples are cations of the following elements: H, Li, Na, K, Mg, Ca, La, Ce, Pr, Nd, preferably H, Li, Na, K and Mg. The introduction of the exchangeable cations Me is known to the person skilled in the art; ion exchange processes in which an aqueous metal salt solution is brought into contact with the zeolites are often used (D. W. Breck, "Zeolithe Molecular Sieves, Structure, Chemistry and Use", J. Wiley & Sons, New York, 1974).

Before using the pentasil zeolites in the process according to the invention, the sorbed water phase $yH_2O$ is removed by calcination at from 100° to 500° C.

The process according to the invention is carried out such that the mixture of the isomeric dichlorobenzenes (DCB) is present as a liquid phase in a suitable solvent. It is important for the economy of the process that the solvent employed can be separated from the dichlorobenzene by a simple distillation. The contents of the individual isomers may vary within wide limits. Preference is given to mixtures comprising at least 50% by weight of m-DCB, mixtures containing more than 70% by weight of m-DCB being particularly preferred.

Suitable solvents for the claimed process are one or more solvents from the aforementioned groups. Examples are: cyclopentane, methylcyclopentane, cyclohexane, methylcyclohexane, dimethylcyclohexane, isopropyl cyclohexane, menthane, decalin, tetralin, o-xylene, m-xylene, isopropylbenzene, 1,3,5-trimethylbenzene, diethylbenzene, chlorotoluene, the isomeric dichlorotoluenes and the isomeric trichlorobenzenes.

Preferred solvents for the process according to the invention belong to the group of cyclic aliphatic hydrocarbons having 5 to 12 carbon atoms, alkyl-substituted aromatic hydrocarbons having 8 to 10 carbon atoms, which contain 1 to 3 alkyl radicals which in each case contain up to 3 carbon atoms but together not more than 4 carbon atoms, and also the chlorinated benzene derivatives having 6 to 8 carbon atoms and 1 to 3 chlorine atoms, with the exception of ethylbenzene, chlorobenzene and dichlorobenzene. Particularly preferred solvents are cyclohexane, o-xylene, m-xylene, mesitylene, 1,2,4-trichlorobenzene and 3,4-dichlorotoluene.

The solvent or a mixture of a plurality of solvents is used in an amount of from 50 to 250% by weight, preferably from 50 to 100% by weight, based on the weight of the dichlorobenzene mixture.

The amount of the mixture of the dichlorobenzenes to be separated, based on the amount of the pentasil zeolite, is restricted by the intended separation effect, which per separation step and stage becomes less the larger the amount of dichlorobenzene mixture. In general from 0.05 to 2, preferably from 0.1 to 1, and particularly preferably from 0.2 to 0.8 amount units of dichlorobenzene are used per amount unit of pentasil zeolite.

The process according to the invention is carried out at a temperature of from 20° to 250° C., preferably from 20° to 200° C. The pressure is not critical for the process according to the invention; in general therefore the process is carried out at atmospheric pressure in order to simplify the reaction apparatus. However, the process can also be carried out at superatmospheric pressure if the solvent is used at an operating temperature above its boiling point.

The mixture of m- and p-dichlorobenzene, dissolved in one of the aforementioned solvents, is brought into contact with the pentasil zeolite in powder or granule form. The more strongly adsorbed component p-dichlorobenzene is removed highly selectively from the mixture. After the end of the adsorption the liquid phase is separated from the zeolite. This liquid phase contains m-dichlorobenzene in highly enriched form. This liquid phase (solvent and remaining dichlorobenzene isomer) is worked up as such. The adsorbed p-dichlorobenzene can be removed from the pentasil zeolite by desorption known per se.

The adsorbed p-dichlorobenzene can be obtained by removing it from the zeolite. In this procedure the zeolite is simultaneously regenerated and can be re-used for the process according to the invention. The desorption can be carried out as desired by altering the pressure and/or temperature or by using an auxiliary having a displacement action. Auxiliaries that may be used are for example hydrogen, nitrogen or alkanes such as methane or ethane. Also suitable for the process according to the invention are benzene, toluene, p-xylene, ethylbenzene and also chlorobenzene and p-chlorotoluene, and in addition polar solvents such as alcohols, for example methanol, ethanol and propanol; ethers, for example diethyl ether, tetrahydrofuran; esters, for example ethyl acetate, butyl acetate, or aliphatic amines, for example triethylamine. Preferred auxiliaries are nitrogen, benzene, toluene, p-xylene, ethylbenzene, chlorobenzene, p-chlorotoluene and methanol. Particularly preferred are nitrogen, benzene, toluene, p-xylene and chlorobenzene. The auxiliaries may be used at temperatures of from 20° C. to 300° C. When auxiliaries that are liquid at room temperature are used for the desorption, the p-isomer is then separated by distillation from the eluant. It is self-evident that only auxiliaries that do not react with the adsorbate are suitable as eluants.

The process can be carried out in a conventional apparatus, known to the person skilled in the art, for separation by means of adsorption. Apparatus permitting a continuous or batchwise operation is suitable. The shape and dimensions of this adsorption apparatus can be optimised and are not, per se, the subject of this invention. In the following examples the quality of the adsorption properties is given by the adsorptive selectivity $\alpha$, which is defined as follows:

$$\alpha_{A/B} = \frac{(\% \text{ by weight } A/\% \text{ by weight } B)_{adsorbed\ phase}}{(\% \text{ by weight } A/\% \text{ by weight } B)_{non\text{-}adsorbed\ phase}}$$

If the selectively adsorbed component p-dichlorobenzene among the dichlorobenzene isomers is denoted by A and the less well adsorbed component m-dichlorobenzene is denoted by B, then the higher the value $\alpha_{A/B}$ the better the separation.

The advantage of the process lies in the extremely high selectivity for the separation of p-dichlorobenzene.

EXAMPLES 1 to 4

In order to determine the adsorption selectivities, 5 g of a 10% strength solution of a mixture of 75% by weight of m-dichlorobenzene (m-DCB) and 25% by weight of p-dichlorobenzene (p-DCB) in 1,2,4-trichlorobenzene were in each case brought into contact with 2.5 g of powdered zeolite and stirred for 1 hour at 25° C. The solution was then separated from the zeolite and investigated by gas chromatography after adding chlorobenzene as internal standard. The results are shown in Table 1.

Comparative Example 1

For this purpose two zeolites of the faujasite type K-Y and Ag,K-Y were prepared, according to the instructions given in U.S. Pat. No. 4,571,441. 2.5 g of a liquid phase mixture of n-nonane, p-DCB, m-DCB and o-dichlorobenzene (o-DCB) were added in a ratio of 1:1:3:3 to 2 g of each adsorbent. Moistened adsorbent without any supernatant liquid phase was obtained, and accordingly the analysis by gas chromatography specified in U.S. Pat. No. 4,571,441 was not possible.

Comparative Examples 2 and 3

For this purpose the zeolites from Comparative Example 1 were also investigated as regards their selectivity according to the method given in Examples 1 to 4; for the results, see Table 1, V2 and V3.

Comparative Examples 4 and 5

A LiX type zeolite prepared in a similar manner to that described in EP 0,334,025 was subjected to a static test according to Examples 1–4 in order to determine its selectivity with respect to p-DCB. However, in contrast to the examples according to the invention, the solvent toluene used in EP 0,334,025 was employed instead of 1,2,4-trichlorobenzene. This static test was carried out at 25° C. (V4) and at 80° C. (V5). The results are shown in Table 1. Static tests carried out in this way serve to help the person skilled in the art, as mentioned above, find suitable adsorbent/solvent systems for the separation, which can then be implemented in continuous or batchwise procedures, as described for example in aforementioned EP 0,334,025. If a selected adsorbent-/solvent system does not exhibit any separation effect in the static test, then the person skilled in the art will not consider using this system for a continuous or batchwise process.

TABLE 1

| Example | Adsorbent | % by weight m-DCB | % by weight p-DCB | $\alpha_{p/m}$ |
|---------|-----------|-------------------|-------------------|----------------|
| 1 | H-ZSM 5 | 99.6 | 0.4 | 1618 |
| 2 | Na-ZSM 5 | 99.8 | 0.2 | 755 |
| 3 | K-ZSM | 99.2 | 0.8 | 68 |
| 4 | Mg-ZSM 5 | 97.5 | 2.5 | 93 |
| V1 | Ag, K-Y | analysis by gas chromatography not possible (see description) | | |
| V2 | K-Y | 76.3 | 23.7 | 2 |
| V3 | Ag, K-Y | 75.1 | 24.9 | 1 |
| V4 | Li-X | 75.0 | 25.0 | 1 |
| V5 | Li-X | 75.0 | 25.0 | 1 |

The Comparative Examples 2 and 3 show separation factors that differ only slightly from 1. No separation of the isomeric dichlorobenzenes is achieved with Ag,K-Y, and only a very slight separation of the p-isomer is achieved with K-Y. The separation factors that were achieved with the adsorbent/solvent combinations according to the invention are of several orders of magnitude higher than those achieved in the comparative examples with the substance systems on which they are based. Also, when using Li-X and toluene as solvent (V4 and V5), no separation of the isomeric dichlorobenzenes is achieved.

Examples 5 to 9 and Comparative Example 6

In order to determine the adsorption selectivities depending on the solvent, 10 g of a 5% strength solution of the mixture of 75% by weight of m-DCB and 25% by weight of p-DCB were in each case stirred with 2 g of Na-ZSM 5 in powder form for 1 hour at 25° C. The solution was then separated from the zeolite and investigated by gas chromatography after adding an internal standard. The results are shown in Table 2

TABLE 2

| Example | Solvent | % by weight m-DCB | % by weight p-DCB | $\alpha_{p/m}$ |
|---------|---------|-------------------|-------------------|----------------|
| 5 | Cyclohexane | 98.8 | 1.2 | 876 |
| 6 | o-Xylene | 96.5 | 3.5 | 26 |
| 7 | m-Xylene | 99.2 | 0.8 | 664 |
| 8 | Mesitylene | 99.6 | 0.4 | 710 |
| 9 | 3,4-Dichlorotoluene | 99.3 | 0.7 | 129 |
| V6 | Chlorobenzene | 75.0 | 25.0 | 1 |

Table 2 shows clearly the influence of the solvents used in the process according to the invention on the quality of the separation result. When chlorobenzene is used as solvent, which is described in U.S. Pat. No. 4,571,441 as a suitable solvent for separating the isomeric dichlorobenzenes, neither of the two isomers is adsorbed, and the separation factor is 1.

What is claimed is:

1. Process for separating mixtures of m- and p-dichlorobenzene having at least 50% by weight of m-dichlorobenzene, by treating such mixtures in the liquid phase with a pentasil zeolite, the amount of dichlorobenzene treated being 0.05 to 2 times the amount of pentasil zeolite used, wherein the mixture is treated in from 50 to 25% by weight of a dichlorobenzene mixture of a solvent from the group of cyclic saturated hydrocarbons having 5 to 15 carbon atoms, alkyl-substituted aromatic hydrocarbons having 8 to 12 carbon atoms, and halogen-substituted aromatic hydrocarbons having 6 to 10 carbon atoms and 1 to 3 halogen atoms or a mixture of a plurality thereof, with the exception of the solvents ethylbenzene, chlorobenzene, p-xylene, p-chlorotoluene and dichlorobenzene, at from 20° to 200° C. and wherein said pentasil zeolite contains, as exchangeable cations, protons, cations of the first or second main group of the Mendeleev Periodic System of the Elements, cations of the rare earth metals or a mixture of a plurality thereof, the enriched m-dichlorobenzene is removed as filtrate, and p-dichlorobenzene is obtained by desorption of the pentasil zeolite.

2. The process of claim 1, wherein the following structure types are used as pentasil zeolites: ZSM 5, ZSM 11, ZSM 8, ZSM 5/ZSM 11-intermediates, Zeta 1, Zeta 3, ZBM 10, Ultrasil, Ultrazet, TZ-01, NU-4, NU-5, AZ-1.

3. The process of claim 2, wherein the following structure types are used as pentasil zeolites: ZSM 5, ZSM 8, ZSM 11 and ZSM 5ZSM 11-intermediates.

4. The process of claim 3, wherein the following structure types are used as pentasil zeolites: ZSM 5 and ZSM 11.

5. The process of claim 1, wherein mixtures containing more than 70% by weight of m-dichlorobenzene are used.

6. The process of claim 1, wherein one or more solvents from the group of cyclic saturated hydrocarbons having 5 to 12 carbon atoms, alkyl-substituted benzenes having 8 to 10 carbon atoms and 1 to 3 alkyl radicals which in each case contain up to 3 carbon atoms but together not more than 4 carbon atoms, and also the chlorinated benzene derivatives having 6 to 8 carbon atoms and 1 to 3 chlorine atoms is/are used, with the exception of ethylbenzene, chlorobenzene and dichlorobenzene.

7. The process of claim 6, wherein cyclohexane, o-xylene, m-xylene, mesitylene; 1,2,4-trichlorobenzene, 3,4-dichlorotoluene or a mixture of a plurality thereof is used.

8. The process of claim 1, wherein from 0.1 to 1 amount units of dichlorobenzene mixture is used per amount unit of pentasil zeolite.

9. The process of claim 7, wherein from 0.2 to 0.8 amount units of dichlorobenzene mixture is used per amount unit of pentasil zeolite.

* * * * *

UNITED STATES PATENT AND TRADEMARK OFFICE
CERTIFICATE OF CORRECTION

PATENT NO. : 5,386,067
DATED : January 31, 1995
INVENTOR(S) : Pentling, et al.

It is certified that error appears in the above-identified patent and that said Letters Patent is hereby corrected as shown below:

Col. 6, line 58   After " 5 " insert -- / --

Col. 8, line 3    After " to " delete " i " and substitute -- 1 --

Col. 8, line 6    Delete claim " 7 " and substitute -- claim 8 --

Signed and Sealed this

Second Day of May, 1995

Attest:

BRUCE LEHMAN

*Attesting Officer*     *Commissioner of Patents and Trademarks*